United States Patent [19]

Poindexter et al.

[11] 4,414,213
[45] Nov. 8, 1983

[54] DIHYDROPYRIDYL CYCLIC IMIDATE ESTERS AND THEIR PHARMACEUTICAL USE

[75] Inventors: Graham S. Poindexter; David L. Temple, Jr., both of Evansville, Ind.

[73] Assignee: Mead Johnson & Company, Evansville, Ind.

[21] Appl. No.: 360,758

[22] Filed: Mar. 22, 1982

[51] Int. Cl.³ .................. A61K 31/44; C07D 211/90; C07D 263/14
[52] U.S. Cl. .................. 424/248.5; 424/248.51; 424/248.54; 424/248.55; 424/263; 544/96; 546/256; 546/273; 546/275
[58] Field of Search .................. 544/96; 546/256, 273, 546/275; 424/248.5, 248.51, 248.54, 248.55, 263

[56] References Cited

U.S. PATENT DOCUMENTS

| | | | |
|---|---|---|---|
| 3,485,847 | 12/1969 | Bossert et al. | 424/266 |
| 3,488,359 | 1/1970 | Bossert et al. | 424/266 |
| 3,511,847 | 5/1970 | Loev et al. | 424/266 |
| 3,985,758 | 10/1976 | Murakami et al. | 424/266 |
| 4,096,270 | 6/1978 | Teulon et al. | 424/266 |
| 4,220,649 | 9/1980 | Kojima et al. | 424/266 |

OTHER PUBLICATIONS

Meyers et al., Heterocycles, vol. 11, pp. 133–138 (1978).
Prous et al., Drugs of the Future, vol. VI, No. 7, (1981) pp. 427–440.

*Primary Examiner*—Henry R. Jiles
*Assistant Examiner*—Bernard Dentz
*Attorney, Agent, or Firm*—Richard P. Ryan; Robert H. Uloth

[57] ABSTRACT

A series of 1,4-dihydropyrid-5-yl cyclic imidate esters have been prepared possessing the general formula

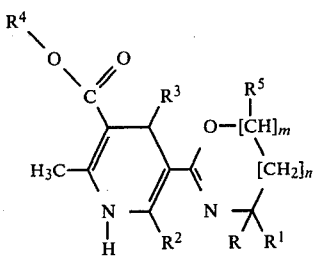

wherein R and $R^1$ are independently selected from hydrogen, lower alkyl or alkoxyalkyl groups; $R^2$ is lower alkyl, aryl, or hetaryl; $R^3$ is cycloalkyl, aryl or hetaryl, generally with electron-withdrawing substituents; $R^4$ is lower alkyl, alkoxyalkyl, aminoalkyl, haloalkyl, or dialkylaminoalkyl; $R^5$ is lower alkyl or aryl; m is 0 or 1; and n is 0, 1, or 2. Compounds of this series demonstrate blockage of calcium ion flux in tissue preparations in vitro and vasodilation in animal testing in vivo.

40 Claims, No Drawings

DIHYDROPYRIDYL CYCLIC IMIDATE ESTERS AND THEIR PHARMACEUTICAL USE

FIELD OF THE INVENTION

The heterocyclic carbon compounds of the present invention are cyclic imidate esters linked directly to the 5-position of substituted 1,4-dihydropyridine moieties and these compounds possess bio-affecting properties.

BACKGROUND OF THE INVENTION

A substantial body of prior art has evolved over the last decade involving compounds of 4-aryl-1,4-dihydropyridine series which have calcium antagonist properties and are useful in the treatment of cardiovascular diseases. These calcium blocking effects appear to mediate vasodilation which makes these compounds useful in treating angina and hypertension. These structures are typified by nifedipine (Formula 1);

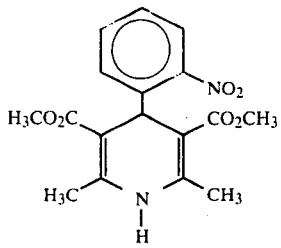
(1)

chemically, 4-(2'-nitrophenyl)-2,6-dimethyl-3,5-dicarbomethoxy-1,4-dihydropyridine. Nifedipine and some related 4-aryl-1,4-dihydropyridines are the subject of U.S. Pat. No. 3,485,847 issued Dec. 23, 1969. Numerous subsequent patents have been granted covering 1,4-dihydropyridines in which other substituent groups have been employed in the various ring positions of the dihydropyridine moiety. The structure of these later patented compounds which relate to the instant invention can be represented by Formula 2.

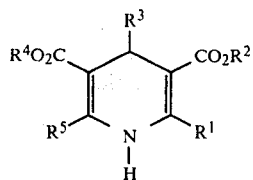
(2)

Bossert, et al, U.S. Pat. No. 3,488,359 patented Jan. 6, 1970 and U.S. Pat. No. 3,574,843 patented Apr. 13, 1971 disclose compounds where the variation involves $R^2$ and $R^4$ being alkoxyalkyl groups.

Murakami, et al, Ger. Offen. No. 2,407,115 disclose compounds where $R^2$ is a disubstituted aminoalkyl group.

Kojima, et al, U.S. Pat. No. 4,220,649 patented Sept. 2, 1980 disclose compounds in which $R^2$ is a pyrrolidine ring.

Loev, et al, U.S. Pat. No. 3,511,847 patented May 12, 1970 list compounds having extensive variation in the nature of $R^3$. Also, the carboxyl groups which bond to $R^2$ and $R^4$ are replaced by carbonyl groups in the disclosure but these compounds are not claimed nor is any preparative method given for their synthesis.

Teulon, et al, U.S. Pat. No. 4,096,270 patented June 20, 1978 disclose dihydropyridines where $R^3$ is a substituted pyridine moiety.

In summary, these and other earlier patented dihydropyridine compounds which relate to the instant invention can be represented by Formula 2. In general, $R^1$, $R^2$, $R^4$, and $R^5$ are alkyl groups or alkyl groups bearing miscellaneous substituents, e.g. amine, ether, mercapto groups, etc. The nature of $R^3$ varies extensively but useful cardiovascular properties seem maximized when this group is an electron withdrawing aryl or heterocyclic moiety.

Meyers and Gabel reported in Heterocycles, Vol. 11, pages 133–138 (1978) a new synthesis of 1,4-dihydropyridines. This synthesis utilizes oxazolines as activating groups to facilitate organo metallic addition to the pyridine ring to yield 1,4-dihydropyridines (Formula 3).

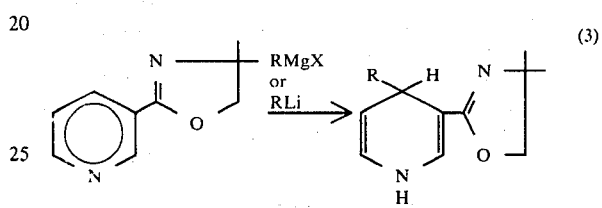
(3)

No utility was given for these compounds and they were usually converted to pyridines under mild oxidative conditions.

SUMMARY AND DETAILED DESCRIPTION OF THE INVENTION

The present invention includes the compounds of Formula I

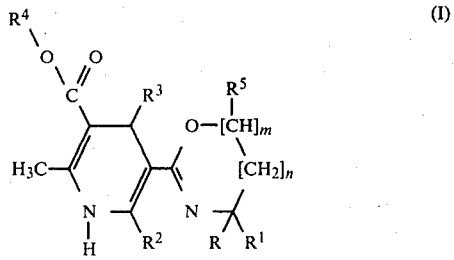
(I)

and the acid addition salts of these substances. In the foregoing structural formula, the symbols R, $R^1$, $R^2$, $R^3$, $R^4$, $R^5$, m, and n have the following meanings. R and $R^1$ are independently selected from hydrogen, lower alkyl or alkoxyalkyl groups, lower alkyl meaning $C_1$ to $C_4$ and alkoxyalkyl referring to a $C_1$ to $C_4$ alkylene chain and a $C_1$ to $C_4$ alkyl group, connected by an oxygen atom; $R^2$ is lower alkyl, phenyl, or thienyl; $R^3$ is cycloalkyl of 5 to 7 carbon atoms, bicycloalkenyl of 7 to 9 carbon atoms, hetaryl such as furanyl, indolyl, pyridyl, thienyl, and the like, aryl meaning phenyl, naphthyl, or substituted phenyl with the substituents comprising acetamino, $C_1$–$C_4$ alkyl, $C_1$–$C_4$ alkoxy, cyano, halogen, hydroxyl, nitro, trifluoromethyl, trifluoromethylsulfonyl, and methylsulfonyl and the like; $R^4$ is lower alkyl or alkoxyalkyl as defined above, aminoalkyl, haloalkyl, or dialkylaminoalkyl referring to a $C_1$ to $C_4$ alkylene chain and $C_1$ to $C_4$ alkyl groups connected by a nitrogen atom; $R^5$ is lower alkyl or aryl; m is 0 or 1; and n is 0, 1, or 2.

The compounds of the present invention can exist as optical isomers and both the racemates of these isomers and the individual racemic modifications themselves are within the scope of the present invention. The racemates can be separated into their individual isomers through well known techniques such as the separation of diastereomeric salts formed with optically active acids, followed by conversion back to the optically active bases.

For potential medical use, the pharmaceutically acceptable acid addition salts are preferred. The phrmaceutically acceptable acid addition salts are those salts in which the anion does not contribute significantly to the toxicity or pharmacological activity of the salt, and as such, they are the pharmacological equivalents of the bases having the foregoing structural formulas. The acid addition salts are obtained either by reaction of an organic base of structure I with an acid, preferably by contract in solution, or by any of the standard methods detailed in the literature and available to any practitioner skilled in the art.

The compounds of this invention were shown to be calcium ion channel blockers on the basis of in vitro pharmacologic testing. Currently, some calcium channel blocking agents are being extensively evaluated in patients with coronary heart disease due to the beneficial cardiovascular effects mediated by these agents.

Biological testing of the subject compounds of Formula I using an in vitro smooth muscle tissue preparation demonstrates that these compounds possess specific blocking action on calcium ion channels. This in vitro calcium ion channel blocker test consists of suspending guinea pig ileal longitudinal smooth muscle strips in baths containing Tyrodes solution maintained at 37° C. aerated with 95% $O_2$–5% $CO_2$. The tissues are equilibrated for 60 minutes prior to the start of all experiments. A single response to carbachol is obtained and used in all experiments as a control maximum. In between successive doses, the tissues are re-equilibrated and washed with Tyrodes solution every 15 minutes. To study the effect of the compounds, the tissues are exposed to the antagonist for 10 minutes prior to the addition of carbachol. For all experiments, only one antagonist at any one concentration is tested in any tissue. Results are expressed as molar concentrations of antagonists which inhibit the muscle response by 50%.

Since calcium antagonism generally inhibits excitation-contraction coupling in vascular smooth muscle, agents of this type usually evoke vasodilation. Testing of selected compounds, for example, ethyl 5-(4,5-dihydro-4,4-dimethyl-2-oxazolyl)-6-ethyl-1,4-dihydro-2-methyl-4-(3-nitrophenyl)-3-pyrimidinecarboxylate and ethyl 5-(4,5-dihydro-2-oxazolyl)-6-ethyl-1,4-dihydro-2-methyl-4-(3-nitrophenyl)-3-pyrimidinecarboxylate; of the instant invention in the ganglion-blocked, angiotensin II-supported rat model (Deitchman, et al., *J. Pharmacol. Methods*, 3, 311–321 (1980)) demonstrated vasodilation with its concommitant lowering of blood pressure.

Additionally, these selected compounds of the instant invention have been examined in vitro and in vivo in laboratory tests developed to predict a drug's potential to protect cardiac tissue from injury due to ischemia. These tests utilize the known relationship between progressive depletion of high energy phosphate and the onset of lethal cell injury in ischemic myocardium. Results of these screening tests demonstrate that these selected compounds possess anti-ischemia action.

Pharmaceutical compositions of this invention, in dosage unit form, contain an effective but non-toxic amount of a compound of Formula I and a suitable pharmaceutical carrier. The amount of the Formula I compound in the composition would range from about 5 mg to about 500 mg. One skilled in the art will recognize that in determining the amounts of the active ingredient in such dosage unit compositions, the activity of the chemical ingredient as well as the size of the host animal must be considered.

Generally, the active ingredients in dosage unit form will be combined with a pharmaceutical carrier. This pharmaceutical carrier may be either a solid or a liquid. Examples of solid carriers would be lactose, magnesium stearate, sucrose, talc, stearic acid, gelatin, gar, pectin, or acacia. Examples of liquid carriers would be peanut oil, olive oil or sesame oil. Similarly, the carrier or diluent may include a time delay material such as glyceryl monostearate or glyceryl distearate alone or with a wax.

A wide variety of pharmaceutical forms can be employed. In examples using a solid carrier, the preparation may be tableted, placed in hard gelatin capsules, or put in the form of a lozenge. The amount of solid carrier will vary widely but generally would be about 25 mg to about 1 g. When a liquid carrier is used, the preparation may be in the form of a soft gelatin capsule, a liquid suspension, or a sterile suspension or solution for parenteral use.

A method of treating via vasodilatation cardiovascular disorders such as angina or hypertension, in accordance with this invention comprises adminstering internally to mammals an effective but non-toxic amount of a compound of Formula I. The active ingredient will preferably be administered in dosage unit form as described above. The route of administration will be oral and/or parenteral.

The compounds of the instant invention are prepared by application of known processes to the appropriate starting materials. Specifically, the present invention utilizes a process for preparation of the compounds of Formula I according to the following reaction scheme.

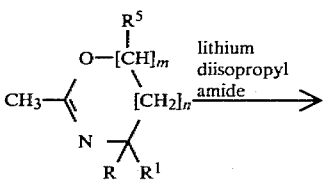

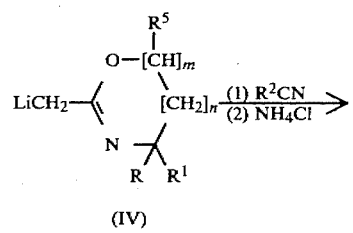

(IV)

-continued

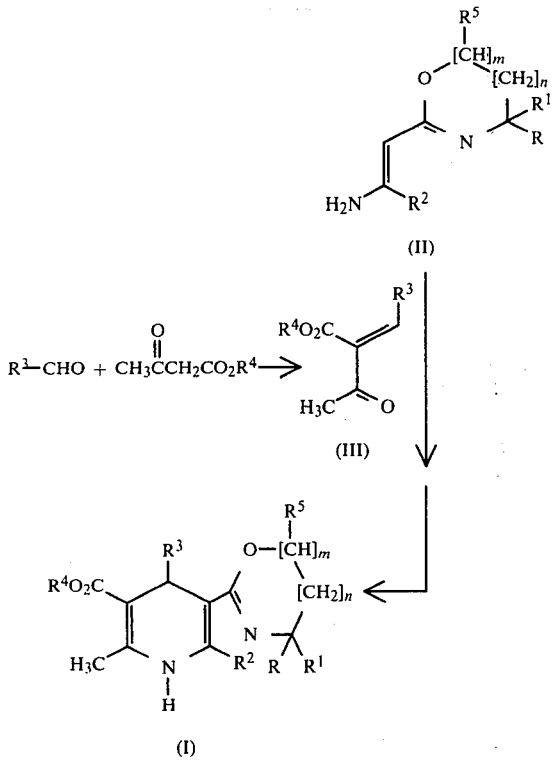

In the foregoing scheme, R, $R^1$, $R^2$, $R^3$, $R^4$, $R^5$, m, and n are as defined in Formula I. The preferred method for making compounds of Formula I consists of refluxing the intermediate adducts II and III in ethanol solution for 18 to 24 hours. Removal of the solvent gives a material which, if it is a solid, is purified by recrystallization and, if it is an oil, is converted to an acid addition salt and then purified. This facile reaction takes place in ordinary laboratory or plant equipment under convenient operating conditions. Preparation of compounds of Formula I according to the process of the invention generally comprises heating II and III neat or in the presence of a wide variety of reaction inert organic solvents. Suitable solvents include but are not limited to benzene, toluene, tetrahydrofuran, dibutylether, butanol, hexanol, methanol, dimethoxyethane, ethyleneglycol, etc. Suitable reaction temperatures are from about 60° to 150° C. No catalyst or condensation agent is required.

The intermediate cyclic imidate ester enamines (II) are conveniently prepared by reacting an appropriately substituted metalated methyl heterocycle (IV) with an appropriate nitrile followed by quenching the reaction with ammonium chloride solution.

The intermediate acetylcinnamate compounds of structure III are prepared utilizing known Knoevenagel condensation reaction conditions. In general, appropriately substituted aldehydes and acetoacetates were condensed to give III.

DESCRIPTION OF SPECIFIC EMBODIMENTS

The compounds which constitute this invention and their methods of preparation will appear more fully from a consideration of the following examples and appended claims which are given for the purpose of illustration only and are not to be construed as limiting the invention in sphere or scope. In examples which follow, used to illustrate the foregoing processes, temperatures are expressed in degrees centigrade and melting points are uncorrected. The proton nuclear magnetic resonance (NMR) spectral characteristics refer to chemical shifts (δ) expressed as parts per million (ppm) versus tetramethylsilane (TMS) as internal reference standard. The relative area reported for the various shifts in the proton NMR spectral data corresponds to the number of hydrogen atoms of a particular functional type in the molecule. The nature of the shifts as to multiplicity is reported as broad singlet (bs), singlet (s), multiplet (m), or doublet (d). Abbreviations employed are DMSO-$d_6$ (deuterodimethylsulfoxide), CDCl$_3$ (deuterochloroform), and are otherwise conventional. The infrared (IR) spectral descriptions include only absorption wave numbers (cm$^{-1}$) having functional group identification value. The IR determinations were employed using potassium bromide (KBr) as diluent. The elemental analyses are reported as percent by weight.

SYNTHESIS OF INTERMEDIATES

A. INTERMEDIATES OF FORMULA II

EXAMPLE 1

2-Amino-1-(4,5-dihydro-2-oxoazolyl)-1-butene

A solution of 2-methyl-2-oxazoline (8.5 g; 0.10 mole) in 100 mL dry tetrahydrofuran (THF) was added via syringe to a stirred suspension of freshly prepared lithium diisopropylamide in 50 mL THF. The suspension was kept stirred under a nitrogen atmosphere at −78° C. for an additional hour after the addition was completed. At this point propionitrile (10 mL; 0.14 mole) was added to the stirred suspension which was then allowed to warm to room temperature with continued stirring. The reaction was then quenched with 25 mL saturated NH$_4$Cl solution. The organic layer was separated and washed with water. The water wash was back extracted with ether and the organic portions combined and washed with brine. The organic solution was dried over K$_2$CO$_3$, filtered, and concentrated to 13 g of yellow liquid. Distillation (90°–95° C. at 1 mm Hg) yielded 6.5 g clear liquid as product (70% yield).

EXAMPLE 2

2-Amino-1-(4,5-dihydro-4,4-dimethyl-2-oxazolyl)-1-propene

A solution of 4,5-dihydro-2,4,4-trimethyl-2-oxazoline (25 g; 0.22 mole) and tetramethylethylenediamine (25.5 g; 0.22 mole) was added to a stirred mixture of lithium diisopropylamide (freshly prepared from 0.23 mole diisopropylamine and 0.23 mole of n-butyl lithium in 100 mL dry THF) kept under a nitrogen atmosphere at −78° C. The resultant whitish suspension was stirred at −78° C. for an additional 2.5 hr. A solution of acetonitrile (15 g; 0.35 mole) in 50 mL THF was added to the stirred reaction mixture which was then allowed to warm to room temperature. The reaction was then quenched with saturated ammonium chloride solution and water added in a quantity sufficient to dissolve all solids in the mixture. A 100 mL portion of ether was added and the resulting layers separated. The organic layer was washed with brine and dried (K$_2$CO$_3$), filtered, and concentrated in vacuo to yield 24.9 g yellow liquid. Distillation afforded a 10% yield or product enamino oxazoline, b.p. 102°–105° C. at 4 mm Hg.

EXAMPLE 3

2-Amino-1-(5,6-dihydro-4,4,6-trimethyl-4H-1,3-oxazin-2-yl)-1butene

To a solution of 11.0 mmoles of lithium diisopropylamide (11.1 g diisopropylamine; 50 mL of 2.4 M n-butyl lithium in n-hexane) in 100 mL THF, kept at 78° C. under a nitrogen atmosphere, was added a solution of 5,6-dihydro-4,4,6-trimethyl-4H-1,3-oxazine (14.1 g; 0.10 mole) in 100 mL THF. The reaction mixture was then allowed to stir at −78° for 2 additional hours at which time a solution of propionitrile (8.3 g; 0.15 mole) in 50 mL THF was added. The reaction mixture was allowed to warm to room temperature and was quenched with 75 mL saturated NH$_4$Cl solution. A 100 mL portion of ether was added, the organic layer was separated, washed with brine, and dried (K$_2$CO$_3$). After the K$_2$CO$_3$ was removed by filtration, the filtrate was concentrated in vacuo to give 21.2 g of a yellow liquid which was distilled to yield 15.5 g (79% yield) of product as a pale yellow oil, b.p. 140° C. at 4 mm Hg.

EXAMPLE 4

2-Amino-1-(4,5-dihydro-4-methoxymethyl-4-methyl-2-oxazolyl)-1-butene

A solution of 4,5-dihydro-2,4-dimethyl-4-hydroxymethyloxazole [10.0 g; 0.78 mole. For synthesis of this hydroxyoxazoline, cf: H. Witte and W. Seeliger, *Angew. Chem., Int. Ed.*, Vol 11, 287 (1972); J. Nys and J. Libeer, *Bull. Soc. Chim. Belges.*, Vol. 65, 377 (1956)] in 100 mL THF was added dropwise to a stirred suspension of sodium hydride (3.6 g of a 57% suspension in mineral oil) in 40 mL dry THF under a nitrogen atmosphere at room temperature. The resulting suspension was stirred for 3 hr under the nitrogen atmosphere and then a solution of methyl iodide (12.1 g; 0.08 mole) in 25 mL THF was added and the mixture allowed to continue stirring overnight. A 100 mL portion of ether was added following which the layers were separated and the organic layer was washed twice with water and then with brine. The organic layer was dried (K$_2$CO$_3$), filtered, and concentrated in vacuo to 8.4 g yellow residual liquor which on distillation afforded 4.4 g (39% yield) of clear liquid product, b.p. 90° C. at 10 mm Hg.

To a stirred, chilled (−78° C.) mixture of lithium diisopropylamide (27 mmoles, prepared from 2.7 g of the amine, 11.3 mL of 2.4 M n-butyllithium in n-hexane) in 10 mL THF was added a solution of the oxazoline intermediate (3.6 g; 25 mm) prepared above. The resulting yellow mixture was stirred at −78° for 1.5 hr at which time propionitrile (2.8 g; 0.05 mole) in 10 mL THF was added. This mixture was allowed to warm to room temperature and was then quenched with a saturated NH$_4$Cl solution. The reaction mixture was then worked up as in the above examples and distillation yielded 1.2 g (25% yield) of the product enamino oxazoline, b.p. 120° at 1 mm Hg.

Some additional examples of intermediates of Formula II which can be prepared using the procedure followed in the foregoing examples are given in Table 1.

TABLE 1

Additional Formula II Intermediates

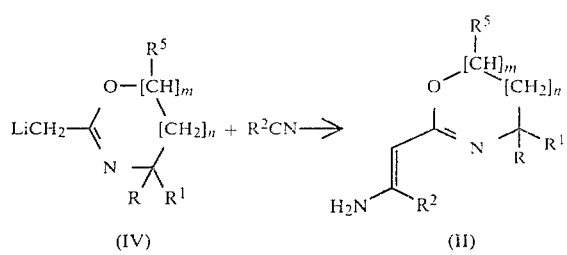

| Ex. | R | R$^1$ | R$^2$ | m | R$^5$ | n | bp (°C./ 0.1 mm) | mp °C. |
|---|---|---|---|---|---|---|---|---|
| 5 | Me | Me | Et | 0 | — | 1 | 70–72 | — |
| 6 | Me | H | Et | 0 | — | 1 | — | — |
| 7 | H | H | Et | 0 | — | 2 | — | — |
| 8 | H | H | Et | 1 | Et | 1 | — | — |
| 9 | MeOCH$_2$ | H | Me | 0 | — | 2 | — | — |
| 10 | H | Me | Ph | 0 | — | 1 | — | — |
| 11 | Me | Me | CHMe$_2$ | 0 | — | 1 | 80 | 58–61 |
| 12 | Me | Me | CMe$_3$ | 0 | — | 1 | — | 132–133 |
| 13 | Me | Me | Ph | 0 | — | 1 | — | 74–75 |
| 14 | Me | Me | 2-thienyl | 0 | — | 1 | 107 | 69–70 |
| 15 | H | H | Et | 1 | Ph | 1 | 175 (at 2.5 mm) | — |

B. INTERMEDIATES OF FORMULA III

EXAMPLE 16

Ethyl α-Acetyl-3-nitrocinnamate

A reaction mixture containing m-nitrobenzaldehyde (151 g; 1.0 mole), ethyl acetoacetate (130 g; 1.0 mole), piperidine (4 mL) and glacial acetic acid (12 mL) in 200 mL benzene was refluxed for 2.5 hr while removing water (19 mL) by means of a Dean Stark trap. The dark brown reaction solution was allowed to cool to room temperature and was then water washed several times and concentrated in vacuo to give a dark yellow solid. This solid was recrystallized from ethanol to yield 182 g (69% yield) of yellow solid, m.p. 103°–106° C. Literature m.p.: S. Ruhemann, *J. Chem. Soc.*, Vol 83, 717 (1903)—m.p. 110° C.

Additional examples of intermediates of Formula III which were prepared using the procedure given in Example 11 are listed in Table 2.

TABLE 2

Additional Formula III Intermediates

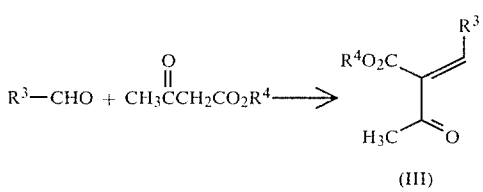

| Ex. | R$^3$ | R$^4$ | b.p. (°C./ 0.1 mm) | m.p. (°C.) |
|---|---|---|---|---|
| 17 | m-nitrophenyl | i-propyl | — | — |
| 18 | m-nitrophenyl | butyl | — | — |
| 19 | m-nitrophenyl | methoxyethyl | — | — |
| 20 | m-nitrophenyl | dimethylaminoethyl | — | — |
| 21 | p-nitrophenyl | ethyl | — | 59.5–61.5 |
| 22 | cyclohexyl | ethyl | 160–170 | — |

TABLE 2-continued
Additional Formula III Intermediates $$R^3-CHO + CH_3\overset{O}{\underset{\|}{C}}CH_2CO_2R^4 \longrightarrow \underset{\underset{H_3C\diagdown\diagup O}{}}{\overset{R^4O_2C\diagdown\diagup R^3}{}}$$

(III)

| Ex. | $R^3$ | $R^4$ | b.p. (°C./ 0.1 mm) | m.p. (°C.) |
|---|---|---|---|---|
| 23 | 1-naphthyl | ethyl | 120–130 | — |
| 24 | 3-indolyl | ethyl | — | 121–122.5 |
| 25 | 2-furanyl | ethyl | 118–120 | — |
| 26 | 2-thienyl | ethyl | 110–120 | — |
| 27 | 3-pyridyl | ethyl | 145–165 | — |
| 28 | 2-bicycloheptenyl | ethyl | 134–140 | — |
| 29 | phenyl | ethyl | 97 | — |
| 30 | m-cyanophenyl | ethyl | 130–160 | — |
| 31 | o-chlorophenyl | ethyl | — | — |
| 32 | m-hydroxy-p-nitrophenyl | ethyl | — | — |
| 33 | o-fluorophenyl | ethyl | 130 | — |
| 34 | m-chlorophenyl | ethyl | 120–123 | — |
| 35 | m-trifluoromethylphenyl | ethyl | 100–110 | — |
| 36 | p-hydroxy-m-nitrophenyl | ethyl | — | — |
| 37 | o-methoxyphenyl | ethyl | — | — |
| 38 | m-methylphenyl | ethyl | 140 | — |
| 39 | p-hydroxy-m-methoxy- | ethyl | — | 110–112 |
| 40 | p-acetomidophenyl | ethyl | — | — |
| 41 | m-methylsulfonyl- | ethyl | — | — |
| 42 | m-trifluoromethylsulfonylphenyl | ethyl | — | — |
| 43 | o-chloro-m-nitrophenyl | ethyl | — | — |
| 44 | o-nitrophenyl | methyl | — | — |
| 45 | m-nitrophenyl | methyl | — | 145–146 |
| 46 | m-nitrophenyl | n-propyl | — | — |
| 47 | m-nitrophenyl | 2-chloroethyl | — | 68–76 |

SYNTHESIS OF PRODUCTS

EXAMPLE 48

Ethyl 5-(4,5-dihydro-4,4-dimethyl-2-oxazolyl)-6-ethyl 1,4-dihydro-2-methyl-4-(3-nitrophenyl)-3-pyridincarboxylate A reaction mixture consisting of ethyl α-acetyl-3-nitrocinnamate (Example 15; 13.2 g, 50.0 mmole), 2-amino-1-(4,5-dihydro-4,4-dimethyl-2-oxazolyl)-1-butene (Example 5; 8.4 g, 50.0 mmoles) and 75 mL ethanol was refluxed for 19 hrs. The mixture was concentrated in vacuo to 21.0 g of a yellow solid which was recrystallized from aqueous ethanol to give 17.4 g (84% yield) yellow crystals, m.p. 162°–163° C.

Anal. Calcd. for $C_{22}H_{27}N_3O_5$: C, 63.91; H, 6.59; N, 10.17. Found: C, 63.90; H, 6.58; N, 10.13.

This and the other dihydro oxalyl dihydropyridine bases of the instant invention are readily convertable to their hydrochloride salts by treating an isopropyl alcohol solution of the base with aqueous HCl followed by conventional work up and purification. Conversion of the above base to its monohydrochloride salt gave a yellow solid, m.p. 234°–235°.

Anal. Calcd. for $C_{22}H_{27}N_3O_5 \cdot HCl$: C, 58.73; H, 6.27; N, 9.34. Found: C, 58.76; H, 6.43; N, 9.36.

NMR (DMSO-$d_6$): 1.21 (6,t [7.0 Hz]); 1.24 (3,s); 1.51 (3,s); 2.39 (3,s); 2.86 (2,m); 4.08 (2,q [7.0 Hz]); 4.58 (2,s); 5.32 (1,s); 7.59 (1,t [8.1 Hz]); 7.97 (2,m); 8.28 (1,m); 10.64 (1,bs); 12.60 (1,bs).

IR (KBr): 1065, 1125, 1230, 1270, 1350, 1440, 1490, 1530, 1585, 1605, 1700, and 2980 cm$^{-1}$.

EXAMPLE 49

Ethyl 5-(4,5-dihydro-2-oxazolyl)-6-ethyl-1,4-dihydro-2-methyl-4-(3-nitrophenyl)-3-pyridinecarboxylate A mixture of 2-amino-1-(4,5-dihydro-2-oxazolyl)-1-butene (Example 1; 5.0 g, 35.7 mmole) and ethyl α-acetyl-3-nitrocinnamate (Example 15; 9.4 g, 35.7 mmole) in 75 mL ethanol was refluxed 23 hrs. Concentration of the reaction mixture in vacuo gave 16.6 g of yellow solid. Recrystallization from ethanol afforded 11.3 (82% yield) yellow solid, m.p. 149°–150° C.

Anal. Calcd. for $C_{20}H_{23}N_3O_5$: C, 62.33; H, 6.02; N, 10.91. Found: C, 62.23; H, 5.96; N, 10.75.

Conversion of the above base to the hydrochloride salt was accomplished by treating an isopropanol solution of the base with 10% aqueous HCl. The reaction solution was filtered, concentrated in vacuo to a yellow solid and recrystallized from methanol to yield yellow solid, m.p. 206°–207° C.

NMR (CF$_3$COOH): 1.42 (6,t [7.4 Hz]); 2.49 (3,s); 3.01 (2,q [7.4 Hz]); 4.11 (2,t [9.0 Hz]); 4.39 (2,q [7.4 Hz]); 5.17 (2,t [9.0 Hz]); 5.20 (1,s); 7.75 (2,m); 8.12 (1,bs); 8.21 (1,m); 8.36 (1,m); 8.71 (1,bs).

IR (KBr): 1070, 1130, 1230, 1260, 1285, 1350, 1435, 1490, 1530, 1590, 1610, 1700, and 2980 cm$^{-1}$.

EXAMPLE 50

Ethyl 5-[4,5-dihydro-4-(methoxymethyl)-4-methyl-2-oxazolyl]-6-ethyl-1,4-dihydro-2-methyl-4-(3-nitrophenyl)-3-pyridinecarboxylate Monohydrochloride A mixture of 2-amino-1-(4,5-dihydro-4-methoxymethyl-4-methyl-2-oxazolyl)-1-butene (Example 4; 0.9 g, 4.6 mmoles) and ethyl α-acetyl-3-nitrocinnamate (Example 15; 1.2 g, 4.0 mmoles) in 10 mL ethanol was refluxed for 23 hrs. The reaction mixture was concentrated in vacuo to a yellow oil which represented the crude product. This crude base was converted to the hydrochloride salt (isopropyl alcohol and 10% aqueous HCl) which upon recrystallization from ethanol yielded 0.25 g (11.3% yield) yellow solid, m.p. 257°–258° C. (dec).

Anal. Calcd. for $C_{23}H_{29}N_3O_6 \cdot HCl$: C, 57.56; H, 6.31; N, 8.76. Found: C, 57.34; H, 6.25; N, 8.46.

NMR (DMSO-$d_6$): 1.22 (6,m); 1.44 (3,s); 2.37 (3,s); 2.78 (2,m); 2.92 (3,s); 3.27 (2,m); 4.10 (2,q [7.4 Hz]); 4.48 (1,d [8.2 Hz]); 4.70 (1,d [8.2 Hz]); 5.31 (1,s); 7.75 (2,m); 8.10 (1,m); 8.28 (1,m); 10.52 (1,bs).

IR (KBr): 1068, 1125, 1225, 1280, 1350, 1440, 1450, 1470, 1495, 1532, 1595, 1620, 1642, and 2980 cm$^{-1}$.

EXAMPLE 51

Ethyl 5-(4,5-dihydro-4,4-dimethyl-2-oxazolyl)-1,4-dihydro-2,6-dimethyl-4-(3-nitrophenyl)-3-pyridinecarboxylate Monohydrochloride A mixture of 2-amino-1-(4,5-dihydro-4,4-dimethyl-2-oxazolyl)-1-propene (Example 2; 2.9 g, 18.8 mmoles) and ethyl α-acetyl-3-nitrocinnamate (Example 15; 4.9 g, 18.8 mmoles) in 20 mL ethanol was refluxed for 18 hrs. The reaction mixture was concentrated in vacuo to an orange oil representing the crude product. This crude base was converted to the hydrochloride salt (isopropanol and 10% aqueous HCl) to yield 4.25 g (52% yield) of yellow crystalline product, m.p. 236° C. (dec) after recrystallization from aqueous ethanol.

Anal. Calcd. for $C_{21}H_{25}N_3O_5 \cdot HCl$: C, 57.87; H, 6.02; N, 9.65. Found: C, 57.71; H, 6.23; N, 9.62.

NMR (DMSO-$d_6$): 1.19 (3,t [6.6 Hz]); 1.24 (3,s); 1.47 (3,s); 2.36 (3,s); 2.44 (3,s); 4.09 (2,q [6.6 Hz]); 4.53 (2,s); 5.20 (1,s); 7.76 (2,m); 8.09 (1,m); 8.25 (1,m); 10.50 (1,bs).

IR (KBr): 1025, 1125, 1240, 1260, 1350, 1445, 1485, 1530, 1590, 1605, 1700, and 2980 cm$^{-1}$.

EXAMPLE 52

Ethyl 5-(5,6-dihydro-4,4,6-trimethyl-4(H)-1,3-oxazine-2-yl)-6-ethyl-1,4-dihydro-2-methyl-4-(3-nitrophenyl)-3-pyridinecarboxylate Monohydrochloride for 20 hr. Concentration in vacuo yielded a yellow solid which was recrystallized from ethanol to afford 8.9 g (81% yield) of yellow solid, m.p. 159°–163° C.

The yellow solid base product prepared above was converted to the hydrochloride salt in the same manner as for the previous examples to yield a yellow solid monohydrochloride salt, m.p. 259°–260° C. (dec).

Anal. Calcd. for $C_{24}H_{31}N_3O_5 \cdot HCl$: C, 60.31; H, 6.75; N, 8.80. Found: C, 60.49; H, 6.78; N, 8.59.

NMR (DMSO-$d_6$): 1.19 (9,m); 1.40 (6,s); 1.90 (2,m); 2.36 (3,s); 2.60 (2,m); 4.06 (2,q [7.0 Hz]); 4.83 (1,m); 4.92 (1,s); 7.68 (2,m); 8.09 (2,m); 9.80 (1,bs).

IR (KBr): 1070, 1105, 1125, 1220, 1265, 1350, 1485, 1530, 1605, 1620, 1695, and 2975 cm$^{-1}$.

Additional examples of products of the instant invention are given in Table 3. These additional products were synthesized using the procedures described in Examples 48–52.

TABLE 3

Additional Formula 1 Products

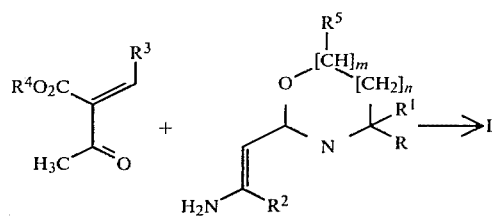

| Ex. | R  | R$^1$    | R$^2$     | R$^3$          | R$^4$                               | m | R$^5$ | n |
|-----|----|----------|-----------|----------------|-------------------------------------|---|-------|---|
| 53  | H  | H        | Et        | 3-NO$_2$Ph     | Me                                  | 0 | —     | 1 |
| 54  | Me | Me       | Et        | 2-furanyl      | Et                                  | 0 | —     | 1 |
| 55  | Me | Me       | Et        | 4-NO$_2$Ph     | Et                                  | 0 | —     | 1 |
| 56  | Me | Me       | Et        | Ph             | Et                                  | 0 | —     | 1 |
| 57  | Me | Me       | Et        | 2-FPh          | Et                                  | 0 | —     | 1 |
| 58  | Me | Me       | i-Pr      | 3-NO$_2$Ph     | Et                                  | 0 | —     | 1 |
| 59  | Me | Me       | t-Bu      | 3-NO$_2$Ph     | Et                                  | 0 | —     | 1 |
| 60  | Me | Me       | Ph        | 3-NO$_2$Ph     | Et                                  | 0 | —     | 1 |
| 61  | Me | Me       | 2-thienyl | 3-NO$_2$Ph     | Et                                  | 0 | —     | 1 |
| 62  | Me | Me       | Et        | 2-Cl—5-NO$_2$Ph| Et                                  | 0 | —     | 1 |
| 63  | Me | Me       | Et        | 3-ClPh         | Et                                  | 0 | —     | 1 |
| 64  | Me | Me       | Et        | 3-CF$_3$Ph     | Et                                  | 0 | —     | 1 |
| 65  | Me | Me       | Et        | 2-thienyl      | Et                                  | 0 | —     | 1 |
| 66  | Me | Me       | Et        | 4-OH—3-MeOPh   | Et                                  | 0 | —     | 1 |
| 67  | Me | Me       | Et        | 3-MePh         | Et                                  | 0 | —     | 1 |
| 68  | Me | Me       | Et        | 1-naphthyl     | Et                                  | 0 | —     | 1 |
| 69  | Me | Me       | Et        | 3-pyridyl      | Et                                  | 0 | —     | 1 |
| 70  | Me | Me       | Et        | 2-ClPh         | Et                                  | 0 | —     | 1 |
| 71  | Me | Me       | Et        | 3-CNPh         | Et                                  | 0 | —     | 1 |
| 72  | Me | Me       | Et        | 2-MeOPh        | Et                                  | 0 | —     | 1 |
| 73  | Me | Me       | Et        | 2-bicycloheptenyl | Et                              | 0 | —     | 1 |
| 74  | Me | Me       | Et        | cyclohexyl     | Et                                  | 0 | —     | 1 |
| 75  | Me | Me       | Et        | 4-AcNHPh       | Et                                  | 0 | —     | 1 |
| 76  | Me | Me       | Et        | 3-OH—4-NO$_2$Ph| Et                                  | 0 | —     | 1 |
| 77  | Me | H        | Me        | 4-isobutylphenyl | Et                                | 1 | Ph    | 1 |
| 78  | H  | CH$_2$OMe| Et        | 4-propoxyphenyl| Et                                  | 0 | —     | 1 |
| 79  | Me | Me       | Et        | 3-ethylphenyl  | MeOCH$_2$CH$_2$                     | 0 | —     | 1 |
| 80  | Me | Me       | Et        | 3-CH$_3$SO$_2$Ph | Me$_2$NCH$_2$CH$_2$               | 0 | —     | 1 |
| 81  | Me | CH$_2$OMe| Et        | 3-CF$_3$SO$_2$Ph | Et                                | 0 | —     | 1 |
| 82  | Me | CH$_2$OMe| Et        | 4-CF$_3$SO$_2$Ph | MeOCH$_2$CH$_2$                   | 0 | —     | 1 |
| 83  | Me | Me       | Et        | 3-indolyl      | Et                                  | 0 | —     | 1 |
| 84  | Me | Me       | Et        | 4-OH—3-NO$_2$Ph| Et                                  | 0 | —     | 1 |
| 85  | H  | H        | Et        | 3-NO$_2$Ph     | i-Pr                                | 0 | —     | 1 |
| 86  | H  | H        | Et        | 3-NO$_2$Ph     | MeOCH$_2$CH$_2$                     | 0 | —     | 1 |
| 87  | H  | H        | Et        | 3-NO$_2$Ph     | ClCH$_2$CH$_2$                      | 0 | —     | 1 |
| 88  | H  | H        | Et        | 3-NO$_2$Ph     | Et                                  | 1 | Ph    | 0 |
| 89  | H  | H        | Et        | 3-NO$_2$Ph     | H$_2$NCH$_2$CH$_2$                  | 0 | —     | 1 |

A mixture of 2-amino-1-(5,6-dihydro-4,4,6-trimethyl-4H-1,3-oxazin-2-yl)-1-butene (Example 3; 4.90 g, 25.0 mmole) and ethyl α-acetyl-3-nitrocinnamate (Example 15; 6.58 g, 25.0 mmole) in 75 mL ethanol was refluxed The physical properties, where available, of the products of the examples listed in Table 3 are given in Table 4.

TABLE 4

Physical Properties - Formula I Products

| Ex. | Name | m.p. (°C.) | Anal. Calcd. | | Found |
|---|---|---|---|---|---|
| 53 | Methyl 5-(4,5-dihydro-2-oxazolyl)-6-ethyl-1,4-dihydro-2-methyl-4-(3-nitrophenyl)-3-pyridine-carboxylate monohydrochloride | 201–202 | C,<br>H,<br>N, | 55.96<br>5.44<br>10.31 | 55.99<br>5.60<br>10.03 |
| 54 | Ethyl 5-(4,5-dihydro-4,4-dimethyl-2-oxazolyl)-6-ethyl-4-(2-furanyl)-1,4-dihydro-2-methyl-3-pyridine-carboxylate | 138.5–140 | C,<br>H,<br>N, | 67.02<br>7.31<br>7.82 | 66.88<br>7.36<br>7.97 |
| 55 | Ethyl 5-(4,5-dihydro-4,4-dimethyl-2-oxazolyl)-6-ethyl-1,4-dihydro-2-methyl-4-(4-nitrophenyl)-3-pyridinecarboxylate monohydrochloride | 246–248 | C,<br>H,<br>N, | 58.73<br>6.28<br>9.34 | 58.36<br>6.63<br>9.40 |
| 56 | Ethyl 5-(4,5-dihydro-4,4-dimethyl-2-oxazolyl)-6-ethyl-1,4-dihydro-2-methyl-4-phenyl-3-pyridine-carboxylate | 147–149 | C,<br>H,<br>N, | 71.71<br>7.66<br>7.60 | 71.69<br>7.66<br>7.48 |
| 57 | Ethyl 5-(4,5-dihydro-4,4-dimethyl-2-oxazolyl)-6-ethyl-4-(2-fluoro-phenyl)-1,4-dihydro-2-methyl-3-pyridinecarboxylate monohydrochloride | 175–177 | C,<br>H,<br>N, | 62.48<br>6.68<br>6.63 | 62.41<br>6.70<br>6.51 |
| 58 | Ethyl 5-(4,5-dihydro-4,4-dimethyl-2-oxazolyl)-1,4-dihydro-2-methyl-6-(1-methylethyl)-4-(3-nitrophenyl)-3-pyridinecarboxylate monohydrochloride | 216–217 | C,<br>H,<br>N, | 59.55<br>6.52<br>9.06 | 59.45<br>6.72<br>9.41 |
| 59 | Ethyl 5-(4,5-dihydro-4,4-dimethyl-2-oxazolyl)-6-(1,1-dimethylethyl)-1,4-dihydro-2-methyl-4-(3-nitro-pyridinecarboxylate | 155–157 | C,<br>H,<br>N, | 65.29<br>7.08<br>9.52 | 64.90<br>7.17<br>9.17 |
| 60 | Ethyl 5-(4,5-dihydro-4,4-dimethyl-2-oxazolyl)-1,4-dihydro-2-methyl-4-(3-nitrophenyl)-6-phenyl-3-pyridinecarboxylate | 112–113 | C,<br>H,<br>N, | 67.67<br>5.90<br>9.11 | 67.73<br>5.86<br>9.04 |
| 61 | Ethyl 5-(4,5-dihydro-4,4-dimethyl-2-oxazolyl)-1,4-dihydro-2-methyl-4-(3-nitrophenyl)-6-(2-thienyl)-3-pyridinecarboxylate monohydrochloride | 143–145 | C,<br>H,<br>N, | 57.20<br>5.21<br>8.34 | 57.17<br>5.31<br>8.06 |
| 62 | Ethyl 4-(2-chloro-5-nitrophenyl)-5-(4,5-dihydro-4,4-dimethyl-2-oxazolyl)-6-ethyl-1,4-dihydro-2-methyl-3-pyridinecarboxylate monohydrochloride | 220–224 | C,<br>H,<br>N, | 54.56<br>5.62<br>8.68 | 54.59<br>5.70<br>8.58 |
| 63 | Ethyl 4-(3-chlorophenyl)-5-(4,5-dihydro-4,4-dimethyl-2-oxazolyl)-6-ethyl-1,4-dihydro-2-methyl-3-pyridinecarboxylate | 170–172.5 | C,<br>H,<br>N, | 65.58<br>6.75<br>6.95 | 65.62<br>6.73<br>6.84 |
| 64 | Ethyl 5-(4,5-dihydro-4,4-dimethyl-2-oxazolyl)-6-ethyl-1,4-dihydro-2-methyl-4-[3-(triflueromethyl)phenyl]-3-pyridinecarboxylate | 78–81 | C,<br>H,<br>N, | 63.30<br>6.24<br>6.42 | 62.95<br>6.29<br>6.12 |
| 65 | Ethyl 5-(4,5-dihydro-4,4-dimethyl-2-oxazolyl)-6-ethyl-1,4-dihydro-2-methyl-4-(2-thienyl)-3-pyridine-carboxylate | 155–158 | C,<br>H,<br>N, | 64.14<br>7.00<br>7.48 | 63.92<br>7.06<br>7.17 |
| 66 | Ethyl 5-(4,5-dihydro-4,4-dimethyl-2-oxazolyl)-6-ethyl-1,4-dihydro-4-(4-hydroxy-3-methoxyphenyl)-2-methyl-3-pyridinecarboxylate | 182–185 | C,<br>H,<br>N, | 66.65<br>7.30<br>6.76 | 66.28<br>7.32<br>6.54 |
| 67 | Ethyl 5-(4,5-dihydro-4,4-dimethyl-2-oxazolyl)-6-ethyl-1,4-dihydro-2-methyl-4-(3-methylphenyl)-3-pyridinecarboxylate | 162–163 | C,<br>H,<br>N, | 72.23<br>7.91<br>7.33 | 72.01<br>7.97<br>7.25 |
| 68 | Ethyl 5-(4,5-dihydro-4,4-dimethyl-2-oxazolyl)-6-ethyl-1,4-dihydro-2-methyl-4-(1-naphthalenyl)-3-pyridinecarboxylate monohydrochloride | 236–238 | C,<br>H,<br>N, | 68.63<br>6.87<br>6.16 | 68.79<br>6.65<br>5.87 |
| 69 | Ethyl 5-(4,5-dihydro-4,4-dimethyl-2-oxazolyl)-6-ethyl-1,4-dihydro-2-methyl-4-(3-pyridinyl)-3-pyridinecarboxylate | 161.5–163.5 | C,<br>H,<br>N,<br>$H_2O$, | 67.94<br>7.39<br>11.32<br>0.49 | 67.70<br>7.48<br>11.22<br>0.5 |
| 70 | Ethyl 4-(2-chlorophenyl)-5-(4,5-dihydro-4,4-dimethyl-2-oxazolyl)-6-ethyl-1,4-dihydro-2-methyl-3-pyridinecarboxylate monohydrochloride | 179–182 | C,<br>H,<br>N,<br>Cl, | 60.15<br>6.43<br>6.38<br>16.14 | 59.78<br>6.18<br>6.40<br>16.13 |
| 71 | Ethyl 4-(3-cyanophenyl)-5-(4,5-dihydro-4,4-dimethyl-2-oxazolyl)-6-ethyl-1,4-dihydro-2-methyl-3-pyridinecarboxylate | 179–181 | C,<br>H,<br>N, | 70.21<br>6.92<br>10.68 | 70.15<br>6.92<br>10.54 |
| 72 | Ethyl 5-(4,5-dihydro-4,4-dimethyl- | 230 | C, | 63.52 | 63.22 |

TABLE 4-continued

Physical Properties - Formula I Products

| Ex. | Name | m.p. (°C.) | Anal. | Calcd. | Found |
|---|---|---|---|---|---|
|  | 2-oxazolyl)-6-ethyl-1,4-dihydro-4-(2-methoxyphenyl)-2-methyl-3-pyridinecarboxylate monohydrochloride |  | H,<br>N, | 7.19<br>6.45 | 7.20<br>6.24 |
| 73 | Ethyl 4-(bicyclo[2.2.1]hept-5-en-2-yl)-5-(4,5-dihydro-4,4-dimethyl-2-oxazolyl)-6-ethyl-1,4-dihydro-2-methyl-3-pyridinecarboxylate | 165–166.5 | C,<br>H,<br>N, | 71.84<br>8.39<br>7.29 | 72.22<br>8.34<br>7.33 |
| 74 | Ethyl 4-cyclohexyl-5-(4,5-dihydro-4,4-dimethyl-2-oxazolyl)-6-ethyl-1,4-dihydro-2-methyl-3-pyridinecarboxylate monohydrochloride | 205–208 | C,<br>H,<br>N, | 64.30<br>8.59<br>6.82 | 64.14<br>8.56<br>6.42 |
| 75 | Ethyl 4-[4-(acetylamino)phenyl]-5-(4,5-dihydro-4,4-dimethyl-2-oxazolyl)-6-ethyl-1,4-dihydro-2-methyl-3-pyridinecarboxylate monohydrochloride | 240.5–241 | C,<br>H,<br>N,<br>H$_2$O, | 60.62<br>7.10<br>8.84<br>2.84 | 60.51<br>7.17<br>8.51<br>2.70 |
| 76 | Ethyl 5-(4,5-dihydro-4,4-dimethyl-2-oxazolyl)-6-ethyl-1,4-dihydro-4-(3-hydroxy-4-nitrophenyl)-2-methyl-3-pyridinecarboxylate | 145.5–146 | C,<br>H,<br>N, | 61.53<br>6.34<br>9.79 | 61.69<br>6.35<br>9.78 |
| 83 | Ethyl 5-(4,5-dihydro-4,4-dimethyl-2-oxazolyl)-6-ethyl-1,4-dihydro-4-(1H—indol-3-yl)-2-methyl-3-pyridinecarboxylate ethanolate hemihydrate | 124.5–125 | C,<br>H,<br>N,<br>H$_2$O, | 68.32<br>7.57<br>9.56<br>2.05 | 68.67<br>7.45<br>9.62<br>1.97 |
| 84 | Ethyl 5-(4,5-dihydro-4,4-dimethyl-2-oxazolyl)-6-ethyl-1,4-dihydro-4-(4-hydroxy-3-nitrophenyl)-2-methyl-3-pyridinecarboxylate monohydrochloride | 134.5–135 | C,<br>H,<br>N, | 56.72<br>6.06<br>9.02 | 56.62<br>6.08<br>8.82 |
| 85 | 1-Methylethyl 5-(4,5-dihydro-2-oxazolyl)-6-ethyl-1,4-dihydro-2-methyl-4-(3-nitrophenyl)-3-pyridinecarboxylate | 160–161 | C,<br>H,<br>N, | 63.17<br>6.31<br>10.52 | 63.15<br>6.38<br>10.27 |
| 86 | 2-methoxyethyl 5-(4,5-dihydro-2-oxazolyl)-6-ethyl-1,4-dihydro-2-methyl-4-(3-nitrophenyl)-3-pyridinecarboxylate monohydrochloride | 190–191 | C,<br>H,<br>N, | 55.82<br>5.80<br>9.30 | 55.65<br>5.77<br>9.30 |
| 88 | Ethyl 5-(4,5-dihydro-5-phenyl-2-oxazolyl)-6-ethyl-1,4-dihydro-2-methyl-4-(3-nitrophenyl)-3-pyridinecarboxylate monohydrochloride | 193–195 | C,<br>H,<br>N, | 62.72<br>5.67<br>8.44 | 62.59<br>5.65<br>8.33 |

What is claimed is:
1. A compound having the formula

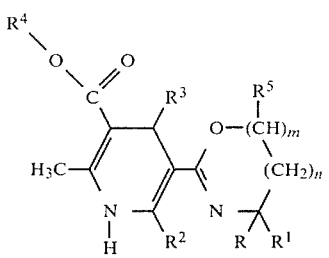

and the pharmaceutically acceptable acid addition salts thereof wherein

R and R$^1$ are independently selected from hydrogen, lower (C$_1$-C$_4$) alkyl or lower alkoxy-lower alkyl groups;

R$^2$ is lower alkyl, phenyl, or thienyl;

R$^3$ is cycloalkyl of 5 to 7 carbon atoms, bicycloalkenyl of 7 to 9 carbon atoms, furanyl, indolyl, pyridyl, thienyl, phenyl, naphthyl, or substituted phenyl with the substituents comprising acetamino, C$_1$-C$_4$ alkyl, C$_1$-C$_4$ alkoxy, cyano, halogen, hydroxyl, nitro, trifluoromethyl, trifluoromethylsulfonyl, and methylsulfonyl;

R$^4$ is lower alkyl, lower alkoxy-lower alkyl, amino-lower alkyl, halo-lower alkyl, or di-lower alkylamino-lower alkyl;

R$^5$ is lower alkyl or aryl;

m is 0 or 1; and n is 0, 1, or 2.

2. The compound of claim 1 wherein R$^2$ is lower alkyl, R$^3$ is 3-nitrophenyl, m is 0, and n is 1.

3. The compound of claim 1, ethyl 5-(4,5-dihydro-4,4-dimethyl-2-oxazolyl)-6-ethyl-1,4-dihydro-2-methyl-4-(3-nitrophenyl)-3-pyridinecarboxylate.

4. The compound of claim 1, ethyl 5-(4,5-dihydro-4,4-dimethyl-2-oxazolyl)-6-ethyl-4-(2-furanyl)-1,4-dihydro-2-methyl-3-pyridinecarboxylate.

5. The compound of claim 1, ethyl 5-(4,5-dihydro-4,4-dimethyl-2-oxazolyl)-6-ethyl-1,4-dihydro-2-methyl-4-(4-nitrophenyl)-3-pyridinecarboxylate.

6. The compound of claim 1, ethyl 5-(4,5-dihydro-4,4-dimethyl-2-oxazolyl)-6-ethyl-1,4-dihydro-2-methyl-4-phenyl-3-pyridinecarboxylate.

7. The compound of claim 1, ethyl 5-(4,5-dihydro-4,4-dimethyl-2-oxazolyl)-6-ethyl-4-(2-fluorophenyl)-1,4-dihydro-2-methyl-3-pyridinecarboxylate.

8. The compound of claim 1, ethyl 5-(4,5-dihydro-4,4-dimethyl-2-oxazolyl)-1,4-dihydro-2-methyl-6-(1-methylethyl)-4-(3-nitrophenyl)-3-pyridinecarboxylate.

9. The compound of claim 1, ethyl 4-(4,5-dihydro-4,4-dimethyl-2-oxazolyl)-6-(1,1-dimethylethyl)-1,4-dihydro-2-methyl)-4-(3-nitrophenyl)-3-pyridinecarboxylate.

10. The compound of claim 1, ethyl 5-(4,5-dihydro-4,4-dimethyl-2-oxazolyl)-1,4-dihydro-2-methyl-4-(3-nitrophenyl)-6-phenyl-3-pyridinecarboxylate.

11. The compound of claim 1, ethyl 5-(4,5-dihydro-4,4-dimethyl-2-oxazolyl)-1,4-dihydro-2-methyl-4-(3-nitrophenyl)-6-(2-thienyl)-3-pyridinecarboxylate.

12. The compound of claim 1, ethyl 5-(4,5-dihydro-5-phenyl-2-oxazolyl)-6-ethyl-1,4-dihydro-2-methyl-4-(3-nitrophenyl)-3-pyridinecarboxylate.

13. The compound of claim 1, ethyl 4-(2-chloro-5-nitrophenyl)-5-(4,5-dihydro-4,4-dimethyl-2-oxazolyl)-6-ethyl-1,4-dihydro-2-methyl-3-pyridinecarboxylate.

14. The compound of claim 1, ethyl 4-(3-chlorophenyl)-5-(4,5-dihydro-4,4-dimethyl-2-oxazolyl)-6-ethyl-1,4-dihydro-2-methyl-3-pyridinecarboxylate.

15. The compound of claim 1, ethyl 5-(4,5-dihydro-4,4-dimethyl-2-oxazolyl)-6-ethyl-1,4-dihydro-2-methyl-4-[3-(trifluoromethyl)phenyl]-3-pyridinecarboxylate.

16. The compound of claim 1, ethyl 5-(4,5-dihydro-4,4-dimethyl-2-oxazolyl)-6-ethyl-1,4-dihydro-2-methyl-4-(2-thienyl)-3-pyridinecarboxylate.

17. The compound of claim 1, ethyl 5-(4,5-dihydro-4,4-dimethyl-2-oxazolyl)-6-ethyl-1,4-dihydro-4-(4-hydroxy-3-methoxyphenyl)-2-methyl-3-pyridinecarboxylate.

18. The compound of claim 1, ethyl 5-(4,5-dihydro-4,4-dimethyl-2-oxazolyl)-6-ethyl-1,4-dihydro-2-methyl-4-(3-methylphenyl)-3-pyridinecarboxylate.

19. The compound of claim 1, ethyl 5-(4,5-dihydro-4,4-dimethyl-2-oxazolyl)-6-ethyl-1,4-dihydro-2-methyl-4-(1-naphthalenyl)-3-pyridinecarboxylate.

20. The compound of claim 1, ethyl 5-(4,5-dihydro-4,4-dimethyl-2-oxazolyl)-6-ethyl-1,4-dihydro-2-methyl-4-(3-pyridinyl)-3-pyridinecarboxylate.

21. The compound of claim 1, ethyl 4-(2-chlorophenyl)-5-(4,5-dihydro-4,4-dimethyl-2-oxazolyl)-6-ethyl-1,4-dihydro-2-methyl-3-pyridinecarboxylate.

22. The compound of claim 1, ethyl 4-(3-cyanophenyl)-5-(4,5-dihydro-4,4-dimethyl-2-oxazolyl)-6-ethyl-1,4-dihydro-2-methyl-3-pyridinecarboxylate.

23. The compound of claim 1, ethyl 5-(4,5-dihydro-4,4-dimethyl-2-oxazolyl)-6-ethyl-1,4-dihydro-4-(2-methoxyphenyl)-2-methyl-3-pyridinecarboxylate.

24. The compound of claim 1, ethyl 4-(bicyclo[2.2.1]hept-5-en-2-yl)-5-(4,5-dihydro-4,4-dimethyl-2-oxazolyl)-6-ethyl-1,4-dihydro-2-methyl-3-pyridinecarboxylate.

25. The compound of claim 1, ethyl 4-cyclohexyl-5-(4,5-dihydro-4,4-dimethyl-2-oxazolyl)-6-ethyl-1,4-dihydro-2-methyl-3-pyridinecarboxylate.

26. The compound of claim 1, ethyl 4-[4-(acetylamino)phenyl]-5-(4,5-dihydro-4,4-dimethyl-2-oxazolyl)-6-ethyl-1,4-dihydro-2-methyl-3-pyridinecarboxylate.

27. The compound of claim 1, ethyl 5-(4,5-dihydro-4,4-dimethyl-2-oxazolyl)-6-ethyl-1,4-dihydro-4-(3-hydroxy-4-nitrophenyl)-2-methyl-3-pyridinecarboxylate.

28. The compound of claim 1, ethyl 5-(4,5-dihydro-4,4-dimethyl-2-oxazolyl)-6-ethyl-1,4-dihydro-4-(1H-indol-3-yl)-2-methyl-3-pyridinecarboxylate.

29. The compound of claim 1, ethyl 5-(4,5-dihydro-4,4-dimethyl-2-oxazolyl)-6-ethyl-1,4-dihydro-4-(4-hydroxy-3-nitrophenyl)-2-methyl-3-pyridinecarboxylate.

30. The compound of claim 1, methyl 5-(4,5-dihydro-2-oxazolyl)-6-ethyl-1,4-dihydro-2-methyl-4-(3-nitrophenyl)-3-pyridinecarboxylate.

31. The compound of claim 1, ethyl 5-(4,5-dihydro-2-oxazolyl)-6-ethyl-1,4-dihydro-2-methyl-4-(3-nitrophenyl)-3-pyridinecarboxylate.

32. The compound of claim 1, ethyl 5-[4,5-dihydro-4-(methoxymethyl)-4-methyl-2-oxazolyl]-6-ethyl-1,4-dihydro-2-methyl-4-(3-nitrophenyl)-3-pyridinecarboxylate.

33. The compound of claim 1, ethyl 5-(4,5-dihydro-4,4-dimethyl-2-oxazolyl)-1,4-dihydro-2,6-dimethyl-4-(3-nitrophenyl)-3-pyridinecarboxylate.

34. The compound of claim 1, ethyl 5-(5,6-dihydro-4,4,6-trimethyl-4H-1,3-oxazin-2-yl)-6-ethyl-1,4-dihydro-2-methyl-4-(3-nitrophenyl)-3-pyridinecarboxylate.

35. The compound of claim 1, 1-methylethyl 5-(4,5-dihydro-2-oxazolyl)-6-ethyl-1,4-dihydro-2-methyl-4-(3-nitrophenyl)-3-pyridinecarboxylate.

36. The compound of claim 1, 2-methoxyethyl 5-(4,5-dihydro-2-oxazolyl)-6-ethyl-1,4-dihydro-2-methyl-4-(3-nitrophenyl)-3-pyridinecarboxylate.

37. A pharmaceutical composition for the treatment of cardiovascular disease such as angina or hypertension comprising from 5 to 500 mg of a compound claimed in claim 1 in combination with a pharmaceutically acceptable, non-toxic inert carrier.

38. The method of exerting a vasodilating effect in a mammalian host which comprises administering to a mammal having a condition in which therapeutic benefit is derived from vasodilation, a non-toxic effective vasodilating dose of a compound as claimed in claim 1.

39. The antihypertensive method which comprises administering to a mammalian host having hypertension a non-toxic antihypertensive effective dose of a compound claimed in claim 1.

40. The anti-ischemia method which comprises administering to a mammalian host, subject to ischemic attack, a non-toxic anti-ischemia effective dose of a compound claimed in claim 1.

* * * * *